United States Patent [19]

Yazaki et al.

[11] Patent Number: 5,994,575
[45] Date of Patent: Nov. 30, 1999

[54] PHENYLENEDIAMINES AND PROCESS FOR PREPARING THE SAME

[75] Inventors: Akira Yazaki; Jiro Yoshida; Yoshiko Niino, all of Takata-gun, Japan

[73] Assignee: Wakunaga Pharmaceutical Co., Ltd., Osaka, Japan

[21] Appl. No.: 09/147,133

[22] PCT Filed: Apr. 10, 1997

[86] PCT No.: PCT/JP97/01233

§ 371 Date: Oct. 15, 1998

§ 102(e) Date: Oct. 15, 1998

[87] PCT Pub. No.: WO97/38971

PCT Pub. Date: Oct. 23, 1997

[30] Foreign Application Priority Data

Apr. 16, 1996 [JP] Japan ................................. 8-093915

[51] Int. Cl.⁶ .................................................. C07C 261/00
[52] U.S. Cl. ............................................................ 560/24
[58] Field of Search ................................................ 560/24

[56] References Cited

FOREIGN PATENT DOCUMENTS

| WO96/12704 | 5/1996 | WIPO | ........................... C07D 215/56 |
| WO96/23775 | 8/1996 | WIPO | ........................... C07D 215/56 |

OTHER PUBLICATIONS

Database CAPLUS on STN, Acc. No. 1995:621678. IWAZAWA et al., 'Preparation of uracil derivative by cyclo-condensation of alkyl 4,4,4–trifluoro–3–methylaminocrotonate with alkyl phenylcarbamate.' JP 07061975 A2 (abstract), 1995.

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

Phenylenediamines represented by general formula (1):

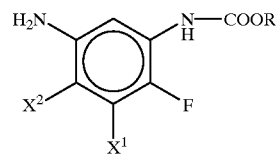

wherein R represents an alkyl group or an optionally substituted aralkyl group, $X^1$ represents a hydrogen atom or a halogen atom, and $X^2$ represents a halogen atom; salts thereof, and a process for preparing the same. The compounds are useful as intermediates for synthesis of pyridonecarboxylic acid derivatives useful as antibacterial agents.

4 Claims, No Drawings

PHENYLENEDIAMINES AND PROCESS FOR PREPARING THE SAME

TECHNICAL FIELD

The present invention relates to phenylenediamines useful as intermediates for synthesis of pyridonecarboxylic acid derivatives or salts thereof which have excellent antibacterial action and can be absorbed well when administered perorally, and to a process for preparing the same.

BACKGROUND ART

Among compounds having a basic skeleton of pyridonecarboxylic acid there have been known a variety of compounds useful as synthetic antibacterial agents, since they have excellent antibacterial activity and a wide antibacterial spectrum. Of these, in the clinical field, as therapeutic agents for infectious diseases there have been widely used compounds such as norfloxacin (Japanese Patent Application Laid-Open (kokai) No. 53-141286), enoxacin (Japanese Patent Application Laid-Open (kokai) No. 55-31042), ofloxacin (Japanese Patent Application Laid-Open (kokai) No. 57-46986), ciprofloxacin (Japanese Patent Application Laid-Open (kokai) No. 58-76667), and tosufluoxacin (Japanese Patent Application Laid-Open (kokai) No. 60-228479).

However, these compounds are not perfectly satisfactory in terms of antibacterial activity, intestinal absorption efficiency, stability in metabolism, and side effects, inter alia, phototoxicity and cytotoxicity.

In view of the foregoing, an object of the present invention is to provide pyridonecarboxylic acid-based antibacterial agents which have satisfactory antibacterial activity, intestinal absorption efficiency, stability in metabolism, and acceptable side effects particularly in terms of phototoxicity and cytotoxicity; and to provide intermediates for synthesis thereof.

DISCLOSURE OF THE INVENTION

The present inventors have conducted earnest studies in an attempt to obtain a compound which may serve as a clinically excellent synthetic antibacterial agent, and have found that pyridonecarboxylic acids represented by the below-described formula (A) have excellent antibacterial activity to Gram-negative and -positive bacteria and remarkably low toxicity and are therefore suitable as synthetic antibacterial agents, and that the compounds (A) can be advantageously produced on an industrial scale through a method in which reaction proceeds according to the below-described reaction scheme via phenylenediamines represented by formula (1), leading to completion of the present invention.

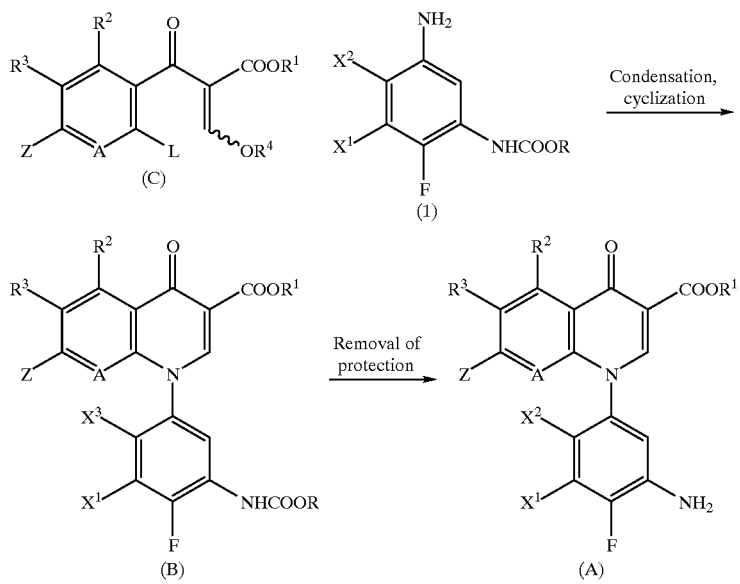

[wherein $R^1$ represents a lower alkyl group; $R^2$ represents a hydrogen atom, a halogen atom, a hydroxy group, a lower alkyl group, or an amino group; $R^3$ represents a hydrogen atom or a halogen atom; $X^1$ represents a hydrogen atom or a halogen atom; $X^2$ represents a halogen atom; Z represents a halogen atom or a saturated cyclic amino group which may have substituents; A represents a nitrogen atom or —CY=(Y represents a hydrogen atom, a halogen atom, a lower alkyl group, or a lower alkoxy group); R represents an alkyl group or an aralkyl group which may have a substituent; $R^4$ represents a lower alkoxy group or a group of —N($R^5$)$R^6$ (each of $R^5$ and $R^6$ represents a lower alkyl group); and L represents a halogen atom].

Briefly, an acrylate ester (C) and a phenylenediamine (1) are condensed and cyclized together to form a compound (B), from which the amino-protective group ( —COOR) is then removed, to thereby obtain a compound (A).

The phenylenediamine compounds (1) used in the reaction are novel compounds; thus they are important intermediates for synthesis in the reaction.

Accordingly, the present invention provides phenylenediamines represented by the above-described formula (1), salts thereof, and a process for preparing the same.

MODES FOR CARRYING OUT THE INVENTION

In the above-described formula (1), alkyl groups represented by R preferably have 1 to 18 carbon atoms.

Specifically, mention may be given of a methyl group, an ethyl group, an n-propyl group, an i-propyl group, an n-butyl group, an i-butyl group, linear or branched pentyl, hexyl, heptyl, octyl, nonyl, decyl, undecyl, dodecyl, tridecyl, tetradecyl, pentadecyl, hexadecyl, and octadecyl groups. Of these, those having 1 to 6 carbon atoms are particularly preferred. Example aralkyl groups represented by R include a benzyl group, a phenylethyl group, and a phenylpropyl group. Of these, the benzyl group is preferred. Example halogen atoms represented by $X^1$ or $X^2$ include a fluorine atom, a chlorine atom, a bromine atom, and an iodine atom. $X^1$ is preferably a hydrogen atom or a fluorine atom, and $X^2$ is preferably a fluorine atom or a chlorine atom.

Example salts of phenylenediamines of formula (1) include salts with mineral acids such as HCl, salts with organic carboxylic acids such as formic acid and acetic acid, and salts with sulfonic acids such as methanesulfonic acid and p-toluenesulfonic acid. Of these, preferred salts are those with methanesulfonic acid and p-toluenesulfonic acid.

The phenylenediamines of formula (1) or their salts may exist not only in the non-solvated form but also as hydrates or solvates. Accordingly, the compounds of the present invention broadly encompass compounds in any crystal system, hydrates of the compounds, and solvates of the compounds.

The compounds (1) of the present invention may be prepared by, for example, the following reaction scheme.

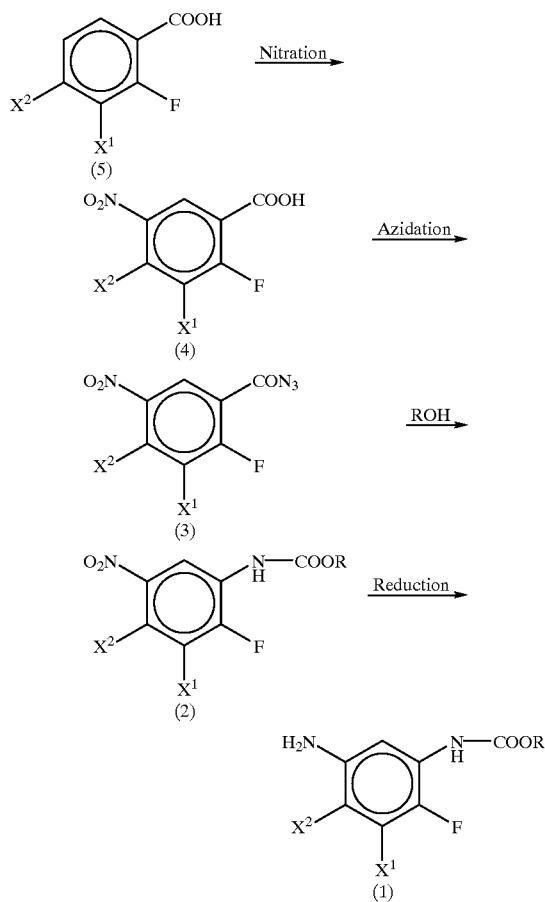

[wherein R, $X^1$, and $X^2$ have the same meanings as defined above].

Briefly, the benzoic acid derivative of formula (5) above is nitrated to obtain a nitrobenzoic acid derivative (4), and this derivative is azidated to form a compound (3). The compound (3) is reacted with an alcohol represented by ROH so as to form a nitroaniline derivative (2), and reduction of nitroaniline derivative (2) produces a phenylenediamine (1).

Next, respective steps will be described in a step-by-step manner.

(1) Preparation of nitrobenzoic acid derivative (4):

Nitrobenzoic acid derivative (4) can be prepared by nitration of compound (5). Nitration may be carried out through use of any customary method generally employed for the nitration of aromatic compounds. Example nitration agents include nitric acid, an acid mixture in which a nitrate and sulfuric acid are combined, and acetyl nitrate. The amount of the acid mixture to be used for the reaction is such that one equivalent to a largely excessive amount of sulfuric acid or nitric acid is employed with respect to one equivalent of compound (5). The reaction is allowed to proceed by, for example, addition of compound (5) to the acid mixture. Preferably, the reaction temperature is −10° C. to 80° C., and the reaction time is 5 minutes to 5 hours.

(2) Preparation of azide derivative (3)

Adization of compound (4) may be carried out by use of a method known per se. For example, either one of the following methods (a) and (b) may be used. (a) The carboxyl group is activated, followed by reaction with an azidation agent. (b) The carboxyl group is activated and hydrazine is reacted to form a hydrozide, followed by reaction with a nitrous acid.

In method (a), the carboxylic group of compound (4) may be activated by use of an acid halide method or an acid mixture anhydride method. A preferred acid halide is an acid chloride. In order to obtain an acid chloride of compound (4), compound (4) is preferably reacted with a halogenation agent such as oxalyl chloride, phosphoryl chloride, thionyl chloride, phosphorus pentachloride, or phosphorus trichloride. This reaction for obtaining an acid halide is preferably carried out, for example, in a solvent such as methylene chloride at a temperature between 0° C. and 100° C., preferably at about room temperature, for one to 48 hours.

The acid mixture anhydride is preferably obtained by reacting compound (4) with ethyl chloroformate or a similar substance.

Example azidation agents to be reacted with the resultant acid halide or acid mixture anhydride include sodium azide and trimethylsilylazide. Azidation is preferably be carried out, for example, in a solvent such as DMF at −20° to 20° C. for 5 minutes to 5 hours.

In the above-mentioned method (b), the thus-obtained acid halide or acid mixture anhydride is reacted with hydrazine hydrate at −20° to 20° C., then with nitrous acid at −20° to 10° C. The reaction for obtaining the hydrazide derivative is preferably carried out, for example, in an ethanol solvent for 5 minutes to 5 hours, whereas the reaction for obtaining the azide derivative is preferably carried out in an aqueous solvent for 5 minutes to 5 hours.

(3) Preparation of nitroaniline derivative (2):

Nitroaniline derivative (2) is obtained through reaction between azide derivative (3) and the aforementioned alcohol ROH. Example alcohols which may be used include benzyl alcohol, ethanol, and 2-methyl-2-propanol. Example solvents include benzyl alcohol, ethanol, 2-methyl-2-propanol, methylene chloride, and DMF. The reaction temperature is preferably between 0° C. and 100° C. and the reaction time is 1–24 hours.

(4) Preparation of phenylenediamine (1)

Phenylenediamine (1) is prepared by subjecting the nitro group of the nitroaniline derivative (2) to a reduction process.

Reduction may be performed by a generally employed method. For example, there may be used a reduction method by use of dissolved metal, in which zinc, iron, tin, tin chloride, etc. may be used in an acidic solution; a reduction method making use of a sulfide such as sodium sulfide, sodium hydrosulfide, or sodium dithionite; or a catalytic reduction method making use of platinum, Raney nickel, platinum-black (Pt—C), palladium-carbon (Pd—C) or a similar substance.

Other than the above-mentioned methods, there may be used another method in which nitroaniline derivative (2) is obtained by subjecting nitrobenzoic acid derivative (4) to a Hofmann rearrangement reaction. For example, nitrobenzoic acid derivative (4) is reacted with thionyl chloride so as to form an acid chloride, and the acid chloride is reacted with ammonia to form an acid amide. The amide is then reacted with hypobromous acid so as to obtain an isocyanate, followed by reaction with an alcohol, to thereby obtain nitroaniline derivative (2). The resultant nitroaniline derivative (2) is transformed into the target phenylenediamine through reduction.

The thus-obtained phenylenediamine (1) may be further processed to form the above-described salts or solvates, as needed.

As described above, through reaction with compound (C), condensation and cyclization, and deprotection, phenylenediamine (1) is transformed into pyridonecarboxylic acid derivatives which are useful antibacterial agents.

EXAMPLES

The present invention will next be described in detail by way of examples, which should not be construed as limiting the invention thereto.

Example 1

(1) 2,3,4-Trifluoro-5-nitrobenzoic acid:

2,3,4-Trifluorobenzoic acid (1 g) was added to sulfuric acid (5 ml), and potassium nitrate (630 mg) was gradually added to the mixture under cooling on ice. The resultant mixture was stirred overnight at room temperature, and the reaction mixture was poured onto crushed ice. The mixture was extracted with diethyl ether, and the organic phase was dried over magnesium sulfate. The solvent was removed through distillation, and n-hexane was added to the residue, to thereby collect the solid of the title compound (1 g) by filtration.
Form: colorless powder
Melting point: 127–135° C.
$^1$H—NMR(CDC$\kappa_3$)$\delta$; 8.67–8.71(m, 1H)

(2) N-Benzyloxycarbonyl-2,3,4-trifluoro-5-nitroaniline:

2,3,4-Trifluoro-5-nitrobenzoic acid (1 g) was added to methylene chloride (10 ml) and N,N-dimethylformamide (several ml), and oxalyl chloride (1.2 ml) was added dropwise to the mixture. The resultant mixture was stirred overnight at room temperature, and the reaction mixture was concentrated under reduced pressure. Methylene chloride (10 ml) and N,N-dimethylformamide (10 ml) were added to the resultant residue, and sodium azide (322 mg) was added to the mixture under cooling on ice. The mixture was stirred at room temperature for one hour, and diethyl ether (20 ml), n-hexane (5 ml), and water (50 ml) were added to the reaction mixture, to thereby collect an organic phase, which was dried over magnesium sulfate. The solvent was removed through distillation, and toluene (10 ml) and benzyl alcohol (1 ml) were added to the residue. The mixture was refluxed overnight. The reaction mixture was concentrated under reduced pressure, and n-hexane was added to the residue, to thereby collect the solid of the title compound (880 mg) by filtration.
Form: yellow powder
Melting point: 136–145° C.
$^1$H—NMR(CDC$\lambda_3$)$\delta$; 5.28(s, 2H), 6.96(brs, 1H), 7.36–7.45(m, 5H), 8.75–8.86(m, 1H)

(3) N-benzyloxycarbonyl-2,3,4-trifluoro-m-phenylenediamine:

Iron (1.2 g) was added to ethanol (20 ml) and water (30 ml), and the mixture was activated with concentrated hydrochloric acid (1 ml) and stirred at 60° C. with heat. A solution of N-benzyloxycarbonyl-2,3,4-trifluoro-5-nitroaniline (800 mg) in ethanol (5 ml) was added dropwise to the above solution, and the mixture was stirred at 80° C. for 10 minutes. The reaction mixture was filtered by use of Celite, and the filtrate was concentrated under reduced pressure. The residue was subjected to column chromatography (silica gel 20 g/n-hexane: ethyl acetate 1:1) for the target fractions, to thereby obtain the title compound (490 mg).
Form: yellow powder
$^1$H—NMR(CDC$\lambda_3$)$\delta$; 5.19(s, 2H), 6.75(brs, 1H), 7.26–7.44(m, 6H)

Example 2

(1) 2,4-Difluoro-5-nitrobenzoic acid:

2,4-Difluoro-5-benzoic acid (151 g) was added to concentrated sulfuric acid (500 ml), and potassium nitrate (114 g) was added portionwise thereto over a period of 30 minutes while the mixture was stirred under cooling on ice. The resultant mixture was stirred for one hour, and the reaction mixture was poured onto crushed ice. The precipitate was collected by filtration, washed with distilled water, and air-dried. Subsequently, the air-dried matter was further dried under reduced pressure over phosphorus pentoxide, to thereby obtain the title compound (164.5 g).
Form: colorless powder
Melting point: 125–130° C.
$^1$H—NMR(CDC$\lambda_3$)$\delta$; 7.20(t, J=10 Hz, 1H), 8.90(t, J=8 Hz, 1H)

(2) N-tert-Butoxycarbonyl-2,4-difluoro-5-nitroaniline:

2,4-Difluoro-5-nitrobenzoic acid (50 g) was added to methylene chloride (400 ml) and N,N-dimethylformamide (several ml). Oxalyl chloride (63 ml) was added dropwise thereto. The resultant mixture was stirred overnight at room temperature, and the reaction mixture was concentrated under reduced pressure. Methylene chloride (80 ml) and N,N-dimethylformamide (90 ml) were added to the residue, and sodium azide (17.6 g) was added portionwise to the mixture under cooling on ice. The mixture was stirred for two hours, and 2-methyl-2-propanol (150 ml) was added to the mixture. The resultant mixture was stirred for 2 hours at room temperature, overnight at 40° C., and for 4 hours at 70° C. The resultant mixture was concentrated under reduced pressure, and ethyl acetate was added to the residue, followed by washing with water twice. The washed matter was dried over magnesium sulfate and concentrated under reduced pressure. Hexane was added to the residue, and through filtration, a solid of the title compound (47 g) was collected.

The filtrate was further concentrated under reduced pressure. The residue was subjected to column chromatography (silica gel 150 g/chloroform) to thereby obtain the title compound (11.5 g). Thus, in total 58.5 g of the title compound was obtained.
Form: yellow powder
Melting point: 87–91° C.

¹H—NMR(CDCλ₃)ϵ; 1.54(s,9H), 6.72(brs,1H), 7.06(t,J=10 Hz, 1H), 8.9–9.01(m,1H)

(3) N-tert-Butoxycarbonyl-2,4-difluoro-m-phenylenediamine:

N-tert-Butoxycarbonyl-2,4-difluoro-5-nitroaniline (20 g) was added to methanol (500 ml) and acetic acid (20 ml). An acetic acid solution of 10% palladium-on-carbon was added thereto, and the resultant mixture was stirred overnight at room temperature in a stream of hydrogen. As the reaction had not been completed, the catalyst was replaced by fresh catalyst and stirring was continued for 2 days. Thereafter, the catalyst was exchanged with palladium-black, and the mixture was stirred overnight at room temperature. The catalyst was filtered off by use of a membrane filter. The filtrate was concentrated under reduced pressure, and ethyl acetate was added to the residue. The residue was washed with a solution of sodium bicarbonate. The washed matter was dried over magnesium sulfate and concentrated under reduced pressure. The residue was subjected to column chromatography (silica gel 150 g/chloroform-ethyl acetate 10 1 ), (silica gel 150 g/chloroform-ethyl acetate 20:1 ). Hexane was added to the residue, and a solid was collected through filtration, to thereby obtain the title compound (9.2 g).

Form: pale brown powder
Melting point: 114–121° C.
¹H—NMR(CDCμ³)δ; 1.51(s,9H), 6.54(brs,1H), 6.78(t,J=11 Hz,1H), 7.54–7.62(m,1H)

Example 3

N-Ethoxycarbonyl-2,4-difluoro-m-phenylenediamine methanesulfonate:

2,4-Difluoro-5-nitrobenzoic acid (6.1 g) was added to dichloromethane (20 ml), and oxalyl chloride (3 ml) and N,N-dimethylformamide (4 drops) were added thereto. The resultant mixture was stirred for 2 hours. Thereafter, the solvent and the excessive reagents were distilled off under reduced pressure. The residue was dissolved in dichloromethane (6 ml), and under stirring and cooling on ice, the resultant solution was added dropwise to sodium azide (2.1 g) in 5 ml of N,N-dimethylformamide. Stirring was continued for 10 minutes, and subsequently, at room temperature for 5 minutes. Diethyl ether (45 ml), n-hexane (15 ml) and distilled water (100 ml) were added, and the resultant mixture was shaken, to thereby separate the organic phase. The organic phase was washed with distilled water (100 ml), dried over magnesium sulfate, and concentrated under reduced pressure. Ethanol (6 ml) was added to two-thirds of the residue. The mixture was heated in a water bath at 80° C. for 2 hours, to thereby obtain a crude solution of N-ethoxycarbonyl-2,4-difluoro-5-nitroaniline in ethanol.

Ethanol (14 ml) was further added to the above-mentioned solution, and methanesulfonic acid (2.0 g) and 10% palladium-on-carbon (200 mg) were added thereto. The resultant mixture was hydrogenated overnight at room temperature. The precipitate was dissolved by the addition of methanol (20 ml), and the catalyst was filtered off. The filtrate was concentrated under reduced pressure, and scales that precipitated were collected through filtration. The scales were washed with a mixture of ethanol and diisopropyl ether, to thereby obtain 4.0 g of the title compound.

Form: fine red crystals

Example 4

N-Benzyloxycarbonyl-2,4-difluoro-m-phenylenediamine:

2,4-Difluoro-5-nitrobenzoic acid (20.3 g) was added to dichlolomethane (60 ml), and oxalyl chloride (10 ml) and N,N-dimethylformamide (15 drops) were added thereto. The resultant mixture was stirred overnight, and the solvent and the excessive reagents were distilled off under reduced pressure. The residue was dissolved in dichloromethane (30 ml), and the mixture was added to N,N-dimethylformamide (15 ml). Under stirring and cooling on ice, sodium azide (7.5 g) was added portionwise to the mixture. Stirring was continued for 10 minutes, and subsequently, at room temperature for an additional 10 minutes. Diethyl ether (100 ml), n-hexane (50 ml), and distilled water (400 ml) were added, and the resultant mixture was shaken, to thereby separate the organic phase. The organic phase was washed with distilled water twice, dried over anhydrous magnesium sulfate, and concentrated under reduced pressure. Benzyl alcohol (12.0 g) was added, and the mixture was concentrated under reduced pressure. Toluene (150 ml) was added thereto. The mixture was heated in a water bath at 40° C. for 2 hours, at 60° C. for 25 hours, and at 100° C. for 1 hour. The solution matter was concentrated under reduced pressure, so that it was gradually solidified. Thus, a crude N-benzyloxycarbonyl-2,4-difluoro-5-nitroaniline was obtained.

Iron powder (84 g) was added to a mixture of distilled water (300 ml) and ethanol (200 ml). Concentrated hydrochloric acid (7 ml) was added portionwise to the mixture under stirring and heating at 80° C. and thereafter, the resultant mixture was stirred for 5 minutes. Subsequently, the entirety of N-benzyloxycarbonyl-2,4-difluoro-5-nitroaniline mentioned above was dissolved in ethanol (100 ml) and the solution was added portionwise so that the mixture refluxed mildly. Thereafter, the resultant mixture was stirred at 80° C. for 15 hours. Benzene (500 ml) was added thereto and the mixture was stirred for 5 minutes. Iron powder was filtered off and the filtrate was washed with ethanol. Distilled water (200 ml) was added thereto and the mixture was shaken, to thereby separate the organic phase. The organic phase was dried over anhydrous magnesium sulfate and while passing through a thin layer of silica gel powder, concentrated under reduced pressure. Colorless scales that precipitated were dispersed into diisopropyl ether. 18.2 g of the title compound was obtained through filtration.

Form: pale brown powder
¹H—NMR(CDCλ₃)δ; 5.20(s,2H), 6.75(brs,1H), 6.79(t,J=10 Hz,1H), 7.30–7.48(m,5H), 7.54–7.68(m,1H)

Reference Example (1) Ethyl 1-(5-tert-butoxycarbonylamino-2,4-difluorophenyl)-8-chloro-6,7-difluoro-1,4-dihydro-4-oxoquinoline-3-carboxylate:

Ethyl 3-chloro-2,4,5-trifluorobenzoylacetate (23 g) was added to ortho-ethyl formate (18.2 g) and acetic anhydride (25 g), and the resultant mixture was refluxed for 3 hours. After having being allowed to cool at room temperature, the mixture was concentrated under reduced pressure. Chloroform (120 ml) was added to the residue, and N-tert-butoxycarbonyl-2,4-difluoro-m-phenylenediamine (20 g) in chloroform-methanol was added dropwise thereto under cooling on ice. After the addition was finished, the resultant mixture was stirred at room temperature for 2 hours. The reaction mixture was concentrated under reduced pressure and hexane was added to the residue. A solid was collected by filtration. Potassium carbonate (11 g) in N,N-dimethylformamide (100 ml) was added to the solid and the mixture was stirred at room temperature for 2 hours. After having being allowed to cool at room temperature, the reaction mixture was poured onto ice water so as to collect precipitate. The precipitate was dissolved in chloroform, and washed with water. The washed matter was dried over magnesium sulfate and subsequently, concentrated under reduced pressure. A solid was collected by filtration and washed with diethyl ether. As a result, 26.1 g of the title compound was obtained.

Form: colorless powder
Melting point: 167–172° C.
$^1$H-NMR(CDCl$_3$)δ; 1.40(t,J=7 Hz,3H), 1.52(s,9H), 4.40(q, J=7 Hz,2H), 6.80(brs,1H), 7.07(t,J=1 Hz,1H), 8.35(t,J=9 Hz,1H), 8.35(s,1H)

(2) 1-(5-Amino-2,4-difluorophenyl)-8-chloro-6,7-difluoro-1,4-dihydro-4-oxoquinoline-3-carboxylic acid:

Ethyl 1-(5-tert-butoxycarbonylamino-2,4-difluorophenyl)-8-chloro-6,7-difluoro-1,4-dihydro-4-oxoquinoline-3-carboxylate (26.1 g) was added to concentrated hydrochloric acid (150 ml) and acetic acid (90 ml) and the mixture was refluxed overnight under heating. After having being allowed to cool at room temperature, the precipitate was collected through filtration, washed with ethanol, and further washed with diethyl ether, to thereby obtain the title compound (18 g).

Form: pale yellow powder
Melting point: 225–226.5° C.
$^1$H—NMR(d$_6$-DMSO)λ; 7.09(t,J=8 Hz,1H), 7.43(t,J=1 Hz,1H), 8.40(t,J=9 Hz, 1H), 8.69(s,1H)

(3) 7-(3-Aminoazetidin-1-yl)-1-(5-amino-2,4-difluorophenyl)-8-chloro-6-fluoro-1,4-dihydro-4-oxoquinoline-3-carboxylic acid:

3-Aminoazetidine dihydrochloride (3.1 g) and N-methylpyrrolidine (6 g) were added to N,N-dimethylformamide (30 ml). 1-(5-Amino-2,4-difluorophenyl)-8-chloro-6,7-difluoro-1,4-dihydro-4-oxoquinoline-3-carboxylic acid (6 g) was added to the mixture under stirring at 80° C. and the mixture was further stirred for 4 hours. After having being allowed to cool at room temperature, ethanol was added to the mixture. The precipitate was collected through filtration, washed with ethanol, and subsequently washed with diethyl ether, to thereby obtain the title compound (4 g).

Form: pale yellow powder
Melting point: >270° C.
$^1$H—NMR(d$_6$-DMSO)μ; 3.75(m, 1H), 4.10(m,2H), 4.66(m, 2H), 5.43(brs,2H), 6.97(t,J=8 Hz,1H), 7.36(t,J=11 Hz,1H), 7.87(d,J=14 Hz, 1H), 8.44(s,1H)

Industrial Applicability

The phenylenediamine compounds (1) of the present invention are useful intermediates for synthesis of pyridonecarboxylic acid derivatives (A) which are useful as antibacterial agents and the like. By the process of the present invention, the phenylenediamine compounds (1) can be prepared advantageously.

We claim:

1. A phenylenediamine represented by formula (1) or a salt thereof:

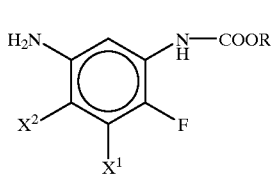

(1)

wherein R represents an alkyl group or an aralkyl group, $X^1$ represents a hydrogen atom or a halogen atom; and $X^2$ represents a halogen atom.

2. A process for preparing a phenylenediamine represented by formula (1) or a salt thereof:

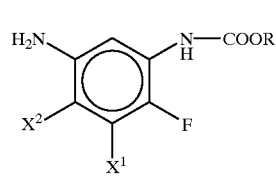

(1)

wherein R represents an alkyl group or an aralkyl group, $X^1$ represents a hydrogen atom or a halogen atom; and $X^2$ represents a halogen atom by reducing a nitroaniline derivative of the following formula (2):

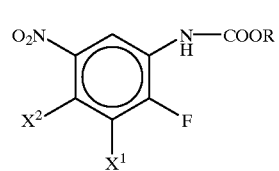

(2)

wherein R, $X^1$, and $X^2$ have the same meanings as defined above.

3. A process for preparing a phenylenediamine represented by formula (1) or a salt thereof:

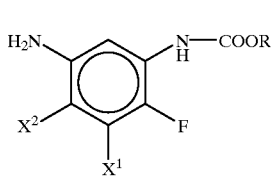

(1)

wherein R represents an alkyl group or an aralkyl group, $X^1$ represents a hydrogen atom or a halogen atom; and $X^2$ represents a halogen atom comprising the steps of:

subjecting a nitrobenzoic acid derivative of formula (4):

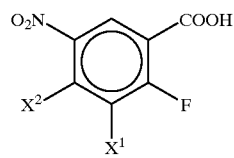
(4)

wherein $X^1$ and $X^2$ have the same meanings as defined above to an azidation reaction so as to obtain a compound having the following formula (3):

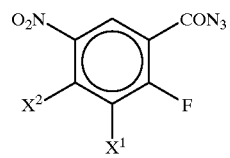
(3)

wherein $X^1$ and $X^2$ have the same meanings as defined above, then reacting the formula (3) compound with an alcohol of formula ROH (wherein R represents an alkyl group or an aralkyl group which may have substituents) to thereby obtain a nitroaniline derivative of formula (2):

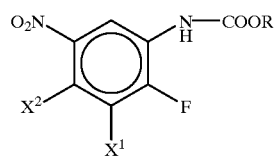
(2)

wherein R, $X^1$, and $X^2$ have the same meanings as defined above, and then reducing the formula (2) compound.

4. A process for preparing a phenylenediamine represented by formula (1) or a salt thereof:

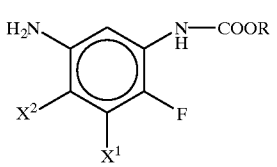
(1)

wherein R represents an alkyl group or an aralkyl group, $X^1$ represents a hydrogen atom or a halogen atom; and $X^2$ represents a halogen atom comprising the steps of:

subjecting a benzoic acid derivative of formula (5):

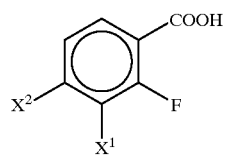
(5)

wherein $X^1$ and $X^2$ have the same meanings as defined above to a nitration reaction so as to obtain a nitrobenzoic acid derivative of formula (4):

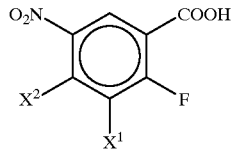
(4)

wherein $X^1$ and $X^2$ have the same meanings as defined above, then subjecting the formula (4) nitrobenzoic acid derivative to an azidation reaction so as to obtain a compound having the following formula (3):

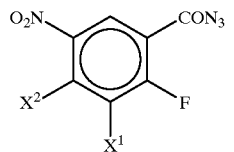
(3)

wherein $X^1$ and $X^2$ have the same meanings as defined above, then reacting the formula (3) compound with an alcohol of formula ROH (wherein R represents an alkyl group or an aralkyl group which may have substituents) to thereby obtain a nitroaniline derivative of formula (2):

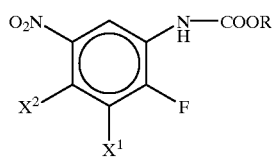
(2)

wherein R, $X^1$, and $X^2$ have the same meanings as defined above, and then reducing the formula (2) compound.

* * * * *